US00PP30285P2

(12) United States Plant Patent
Podaras

(10) Patent No.: US PP30,285 P2
(45) Date of Patent: Mar. 12, 2019

(54) ***BUDDLEIA* PLANT NAMED 'PODCEPT1'**

(50) Latin Name: *Buddleia davidii x Buddleia alternafolia*
Varietal Denomination: Podcept1

(71) Applicant: Peter Podaras, Salem, OR (US)

(72) Inventor: Peter Podaras, Salem, OR (US)

( * ) Notice: Subject to any disclaimer, the term of this patent is extended or adjusted under 35 U.S.C. 154(b) by 0 days.

(21) Appl. No.: 15/732,132

(22) Filed: Sep. 21, 2017

(51) Int. Cl.
*A01H 5/00* (2018.01)

(52) U.S. Cl.
USPC ..... Plt./242

(58) Field of Classification Search
USPC ..... Plt./226, 242
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Buddleia* plant named, 'Podcept1', that is characterized by its short branch internodes, its double, semi-double flowers, and single flowers, its short plant height, its early blooming habit, its numerous inflorescences relative to its plant size, and its inflorescences with semi-indeterminate flowering.

2 Drawing Sheets

Botanical classification: *Buddleia davidii* x *Buddleia alternafolia.*

Variety denomination: 'Podcept1'.

BACKGROUND OF THE INVENTION

The present invention relates to a new and distinct cultivar of *Buddleia davidii* x *Buddleia alternafolia* and will be referred to hereafter by its cultivar name, 'Podcept1'. 'Podcept1' is a new shrub grown for use as an ornamental landscape plant.

The new cultivar of *Buddleia* is a selection from an ongoing breeding program conducted by the Inventor in Salem, Oreg. with the objective of creating new cultivars of *Buddleia* (syn. *Buddleja*) with dwarf plant habits and reduced fertility.

The new variety of *Buddleia*, 'Podcept1', arose from gamma irradiation of seeds collected from unnamed proprietary plants (not patented) of *Buddleia davidii* x *Buddleia alternafolia* in 2014. The exact parent plants are unknown. 'Podcept1' was selected from amongst the resulting seedlings as a single unique plant in 2015.

Asexual propagation of the new cultivar was first accomplished by the Inventor using stem cuttings in Salem, Oreg. in 2015. Asexual propagation by stem cuttings and tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Podcept1' as a unique cultivar of *Buddleia.*

1. 'Podcept1' exhibits short branch internodes.
2. 'Podcept1' exhibits double, semi-double flowers, and single flowers.
3. 'Podcept1' exhibits a short plant height.
4. 'Podcept1' exhibits an early blooming habit.

5. 'Podcept1' exhibits numerous inflorescences relative to its plant size.
6. 'Podcept1' exhibits inflorescences with semi-indeterminate flowering.

'Podcept1' can be compared to the *Buddleia* cultivars 'Blue Chip' (U.S. Plant Pat. No. 19,991) and 'Podaras #9' (U.S. Plant Pat. No. 22,065). 'Blue Chip' is similar to 'Podcept1' in having a short plant height, a long bloom period, and reduced fertility. 'Blue Chip' differs from 'Podcept1' in having narrower and shorter inflorescences that lack indeterminate flowering and flowers that are single only and blue in color. 'Podaras #9' is similar to 'Podcept1' in having an early and long bloom period and a compact and upright plant habit. 'Podaras #9' differs from 'Podcept1' in having inflorescences that lack indeterminate flowering, lighter colored single only flowers, and foliage that is gray-green in color.

BRIEF DESCRIPTION OF THE DRAWINGS

The accompanying colored photographs illustrate the overall appearance and distinct characteristics of the new *Buddleia*. The photographs were taken of a 4 month-old plant as grown outdoors in a 21-cm container in Boskoop, The Netherlands.

The photograph in FIG. 1 provides a side view of the overall plant habit of 'Podcept1' in bloom.

Figure 1:
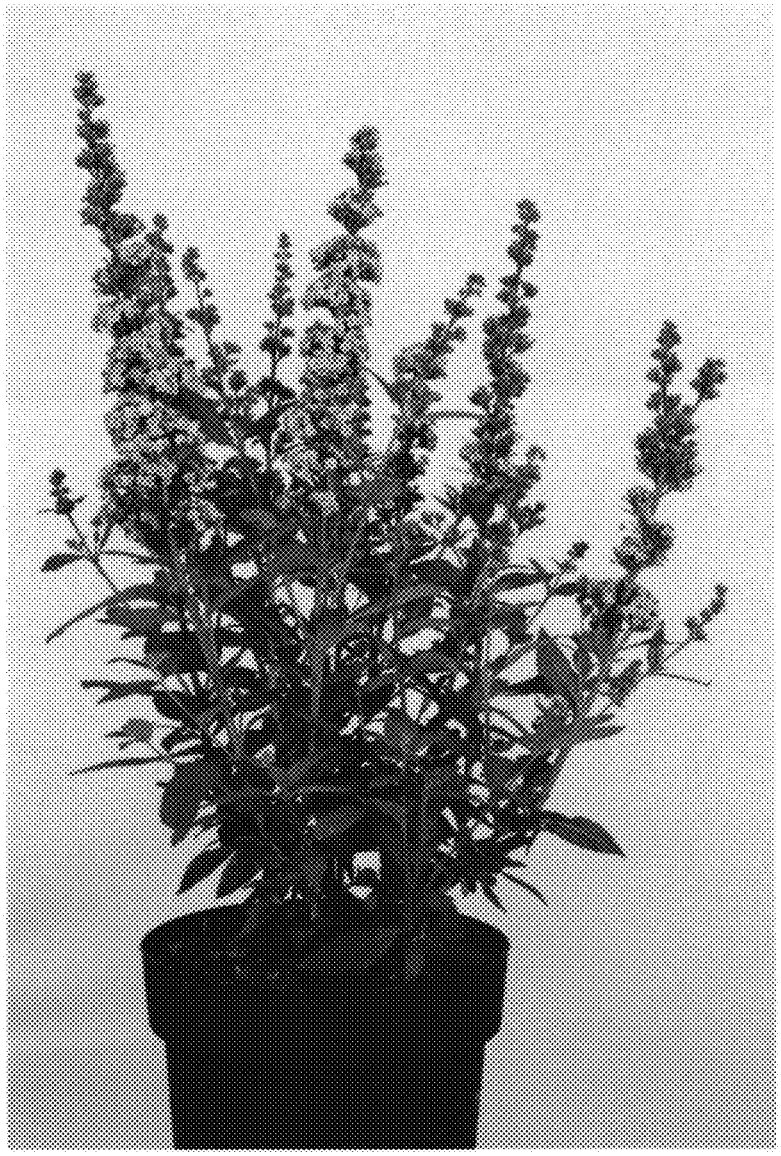
Figure 2:
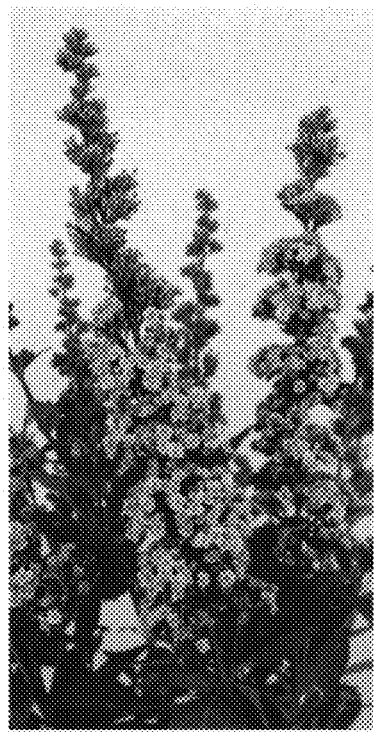

The photograph in FIG. 2 provides a close-up view of the inflorescences of 'Podcept1'.

Figure 3:
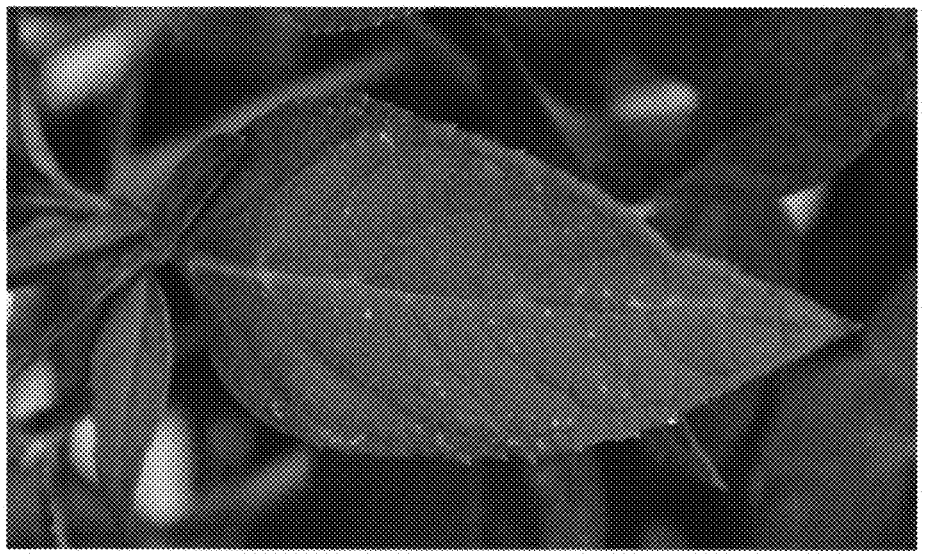

The photograph in FIG. 3 provides a close-up view of the foliage of 'Podcept1'.

The colors in the photographs are as close as possible with the photographic and printing technology utilized and the color values cited in the Detailed Botanical Description accurately describe the colors of the new *Buddleia.*

DETAILED BOTANICAL DESCRIPTION

The following is a detailed description of 4 month-old plants as grown outdoors in 21-cm containers in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms continuously from early spring until late summer in Oregon.

*Plant type*.—Deciduous shrub.

*Plant habit*.—Compact, upright.

*Plant size*.—An average of 54 cm in height and 42 cm in width as grown in a 21-cm container, reaches an average of 91 cm in height and 1.4 m in spread I the landscape.

*Cold hardiness*.—At least in U.S.D.A. Zone 6.

*Diseases and pests*.—No susceptibility and resistance to diseases or pests has been observed.

*Propagation*.—Stem cuttings and tissue culture.

*Root description*.—Fibrous and fine.

*Root development*.—An average of 10 days to initiate roots and six to eight weeks to fully root as a young plant.

*Growth rate*.—Vigorous.

Branch description:

*Branch shape*.—Quadrangular with winged edges, average width of wings is 0.75 mm, Branch color matches stem surface color.

*Branch color*.—Young stems; 144A, mature stems and internodes; between 146C and 152A in color, old stems and bark are 199A to 199B in color.

*Branch strength*.—Moderate.

*Branch size*.—An average of 17.6 cm in length and 5 mm in diameter.

*Branch surface*.—Young branches matte and glabrous, bark smooth.

*Branch aspect*.—Lateral stems held at an average angle of 40° to main stems.

*Branch internode length*.—Average of 3.7 cm.

*Branching*.—Freely branching with 6 main branches and 20 lateral branches per plant.

Foliage description:

*Leaf shape*.—Ovate.

*Leaf division*.—Simple.

*Leaf base*.—Short attenuate.

*Leaf apex*.—Acute.

*Leaf fragrance*.—None.

*Leaf venation*.—Pinnate, color; upper surface 148A, lower surface 148A to 148B.

*Leaf margins*.—Serrate.

*Leaf arrangement*.—Opposite.

*Leaf attachment*.—Petiolate.

*Leaf surface*.—Both sides are smooth and matte, lower surface pubescent.

*Internode length*.—An average of 3.7 cm.

*Leaf size*.—An average of 7.4 cm in length and 3.4 cm in width.

*Leaf quantity*.—An average of 10 per stem.

*Leaf color*.—Young upper surface; 137B, young lower surface; 148C, mature upper surface; NN137A, mature lower surface; 148B.

*Petioles*.—An average of 6 mm in length and 2 mm in diameter, medium to high strength, upper surface color is 144A, lower surface color 146C, upper surface smooth and glabrous, lower side covered in pubescent hairs that are 156D in color.

Inflorescence description:

*Inflorescence type*.—Compound terminal and axial panicles.

*Inflorescence size*.—An average of 24.6 cm in height (including penduncle) and 5.9 cm in diameter.

*Flower fragrance*.—Moderate, typical *Buddleia* scent.

*Lastingness of flowers*.—An average of 10 days, persistent, inflorescence is semi-indeterminate.

*Flower buds*.—Obovate to oblong, average of 4 mm in length and 1.5 mm in diameter, mature bud 84C in color, immature 144B, tipped 197A, surface is matte and covered with pubescence, 156D in color.

*Flower aspect*.—Upright to outward.

*Flower quantity*.—An average of 1,000 flowers per inflorescence.

*Flower type*.—Double, semi-double, or single, salverform in form.

*Flower surface*.—All surfaces glabrous and smooth.

*Flower size*.—An average of 8 mm in height, 1.3 cm in depth, flower throat; 2 mm in diameter, flower tube; 9 mm in length, 1.5 mm in diameter.

*Peduncles*.—An average of 24 cm in length and 2 mm in diameter, held at an average angle of 0° to lateral stem, 146C and tinged 152A in color, strong, smooth and glossy surface.

*Pedicels*.—An average of 2 mm in length and 0.5 mm in diameter, held at an average angle of 45°, 144B in color, moderately strong, surface is glabrous, smooth and matte.

*Calyx*.—Campanulate in shape, an average of 4 mm in depth and 2 mm in diameter.

*Sepals*.—5, 1 whorl, rotate arrangement, fused into a campanulate shape, 4 mm in length, 0.75 mm in width, lower 75% fused, narrow oblanceolate in shape, acute apex, fused base, entire margin, both surface are matte, upper surface glabrous and smooth, lower surface pubescent, color; when opening and fully open upper surface 144B, when opening and fully open lower surface 144B, tipped 197A.

*Petals*.—Average of 6, (varying between 5 and 8), rotate, fused into salverform, 1 whorl, lower 80% fused into tube, spathulate in shape, entire margin, rounded to shallowly emarginated apex, an average of 1.1 cm in length and 3 mm in width, outer and inner surface is glabrous, velvety and matte, color; upper and lower surface when opening 92A, upper and lower surface when fully open 91A, both surfaces fading to 90D, flower throat 23A, flower tube inner side 23A, outer side N77B, tinged with 53D.

*Petaloids*.—Rotate in arrangement, average of 8, 1 whorl, lower 80% fused, spathulate in shape, 1.1 cm in length, 3 mm in width, round apex, fused base, entire margin, both surfaces are smooth, velvety and matte, color when opening upper and lower side 92A, color when fully open upper and lower side 91A, both surfaces fading to 90D.

Reproductive organs:

*Gynoecium*.—1 pistil, 2 mm in length, style; an average of 1 mm in length, 146D in color, stigma; 1 mm in length and 144C in color, ovary is 143C in color.

*Androcoecium*.—Stamens; 5, filament; 0.5 mm in length and 161D in color, anther; sagittate in shape, 1 mm in length, 0.75 mm in width and 161D in color, pollen; none observed.

*Fruit and seed*.—No seeds or fruit produced.

It is claimed:

1. A new and distinct cultivar of *Buddleia* plant named 'Podcept1' as herein illustrated and described.

* * * * *